United States Patent [19]

Darin

[11] Patent Number: 5,026,396
[45] Date of Patent: Jun. 25, 1991

[54] TWO-PIECE INTRAOCULAR LENS

[76] Inventor: John J. Darin, 1250 La Venta Dr., Suite 208, Westlake Village, Calif. 91361

[21] Appl. No.: 519,951

[22] Filed: May 7, 1990

[51] Int. Cl.$^5$ .............................................. A61F 2/16
[52] U.S. Cl. ........................................................ 623/6
[58] Field of Search ............................................ 623/6

[56] References Cited

U.S. PATENT DOCUMENTS 4,608,049 8/1986 Kelman .................................. 623/6
4,764,169 8/1988 Grendahl ............................... 623/6

FOREIGN PATENT DOCUMENTS 3626869 2/1988 Fed. Rep. of Germany .......... 623/6

Primary Examiner—Ronald Frinks
Attorney, Agent, or Firm—Spensley Horn Jubas & Lubitz

[57] ABSTRACT

An implantable intraocular lens assembly composed of a first member having an annular form, an outer periphery and an inner periphery delimiting an opening, and a second member of transparent material having at least one curved surface and an outer periphery. The two members are maintained separated from one another prior to implantation.

The lens assembly is implanted by first implanting the first member separately and then, after implantation of the first member, implanting the second member so that the outer periphery of the second member engages the inner periphery of the first member.

14 Claims, 2 Drawing Sheets

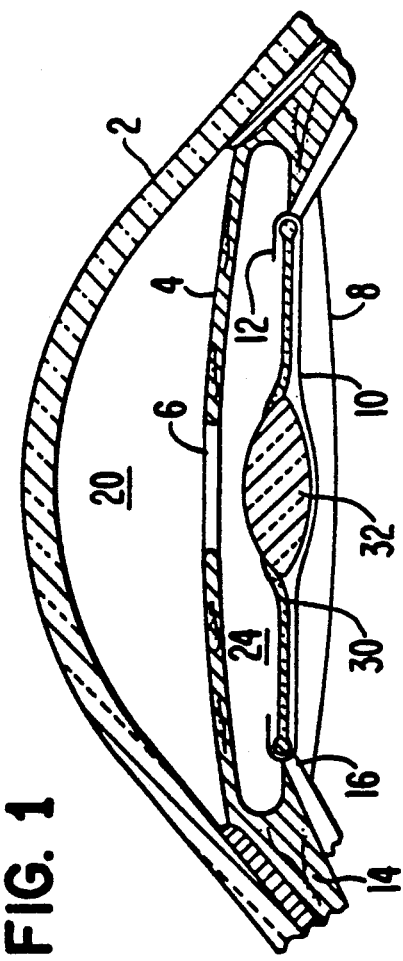
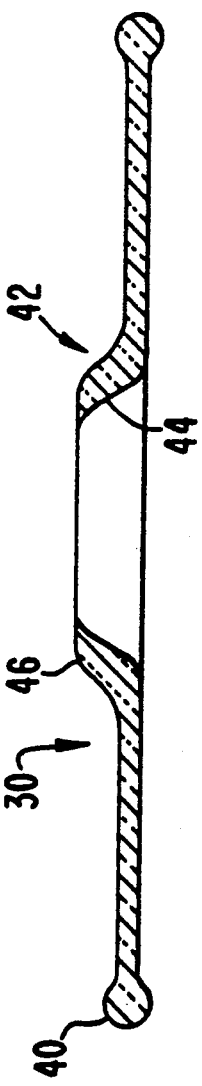
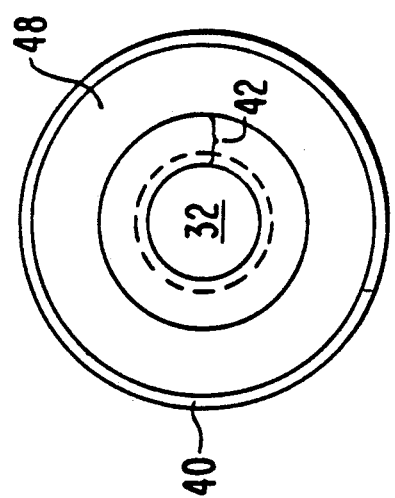
FIG. 1
FIG. 2
FIG. 3
FIG. 4

TWO-PIECE INTRAOCULAR LENS

BACKGROUND OF THE INVENTION

The present invention relates to an intraocular lens, and particularly to a self-centering lens which can be implanted through a very small incision.

When the natural lens is removed from the eye of a patient, for example as a result of the formation of cataracts, it is current practice to replace the natural lens with a synthetic lens. The synthetic lens is generally introduced in a folded state through an incision made in the cornea. It is then placed in the anterior chamber of the eye (forward of the iris) and mounted to it, or in the posterior chamber (behind the iris) and mounted to either the sulcus or fornix. In either case, for a variety of medical reasons, it is desired that the incision be as small as possible.

Since the muscles within the eye cannot change the focus, or curvature, of a synthetic lens in the manner achieved with the natural lens, there has been interest in the provision of a lens having several different refractive powers in order to permit the formation of in-focus images of objects at different ranges. However, in view of the configuration which such a lens must have, it heretofore appeared that such a lens could not be compressed to a size which would permit safe implantation.

SUMMARY OF THE INVENTION

It is an object of the present invention to provide an intraocular lens which can be implanted safely and easily.

Another object of the invention is to make possible safe implantation of an intraocular lens having a variety of optical shapes and refractive elements.

A further object of the invention is to facilitate the fabrication of multifocal intraocular lenses.

The above and other objects are achieved, according to the invention, by an implantable intraocular lens assembly comprising:

a first member having an annular form, an outer periphery and an inner periphery delimiting an opening; and a second member of transparent material having at least one curved surface and an outer periphery;

wherein: the second member is separated from the first member before implantation and is inserted into the opening of the first member after implantation of the first member.

Objects according to the invention are further achieved by a method of implanting the lens assembly defined above as follows:

after a small (3 mm) incision is made in the cornea, a circular tear capsulotomy (capsulorhexis) is performed to remove the anterior capsule;

the cataract is removed through the same 3 mm incision or slit;

cortex material is removed as necessary via asperatean;

via the same incision formed in the cornea, the first member is placed into the eye chamber so that it is held in position in that chamber via its outer periphery. This is achieved either by folding or rolling the first member so it will pass through the small incision; and after implantation of the first member, the second member is implanted via the same incision, into the opening delimited by the inner periphery of the first member so that the outer periphery of the second member engages the inner periphery of the first member.

BRIEF DESCRIPTION OF THE DRAWING

FIG. 1 is a cross-sectional view of the ocular portion of a human eye having a lens assembly according to the invention implanted in the posterior chamber.

FIG. 2 is a cross-sectional view of one component of the lens assembly of FIG. 1.

FIG. 3 is a cross-sectional view of a second component of the lens assembly of FIG. 1.

FIG. 4 is a front view of the lens assembly of FIG. 1.

DESCRIPTION OF THE PREFERRED EMBODIMENTS

Figure 5:
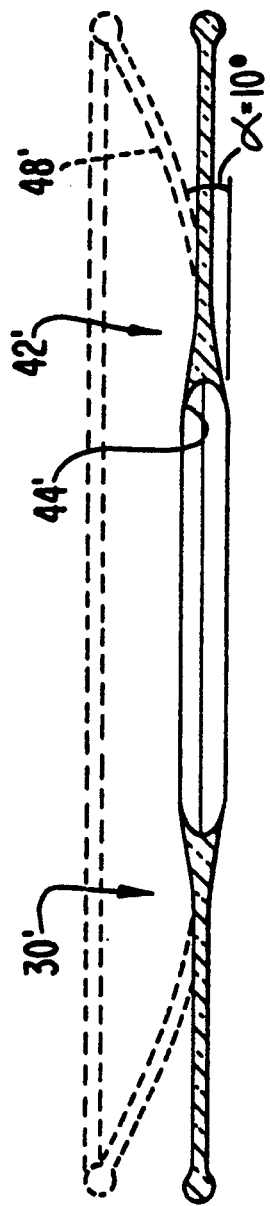
FIG. 5 is a cross-sectional view of a second embodiment of a lens assembly according to the present invention.

FIG. 1 is a side cross-sectional view of the ocular area of the human eye after extracapsular cataract extraction and implantation of a lens according to a preferred embodiment of the present invention. The eye parts illustrated in FIG. 1 include the cornea 2 and the iris 4 which delimits the pupil 6. Posterior to, or behind, iris 4 there is disposed the hyloid membrane 8.

When extracapsular cataract surgery is performed, there further remains within the ocular area the posterior capsule 10 and portions 12 of the anterior capsule. Posterior capsule 10 and the remaining portions 12 of the anterior capsule form what is commonly known as the capsular bag. The posterior capsule is attached to ciliary body 14 by means of zonular fibers 16. The region between cornea 2 and iris 4 is identified as the anterior chamber 20, while the region between posterior capsule 10 and iris 4 is the posterior chamber 24. At the location where anterior capsule portions 12 join to posterior capsule 10, there is created an annular pocket, or fornix.

Preferred embodiments of the present invention are constructed to be implanted in the capsular bag and to be supported in the fornix in a manner to assure accurate and reliable centering of the optical components of the lens.

FIG. 1 further illustrates one embodiment of a lens assembly according to the invention composed of an annular member 30 surrounding and supporting a central lens member 32 having a circular outline.

Annular member 30 is formed of a single piece of material, such as silicone, and has, over the major portion of the region between its inner and outer peripheries, a thin-walled structure enabling member 30 to be folded or rolled into a compact configuration for implantation into posterior chamber 24 via an incision in cornea 2 and then via pupil 6. However, annular member 30 has sufficient shape retention to subsequently expand, after withdrawal of the implantation tool to assume the configuration shown in FIG. 1.

Lens member 32 which, in the illustrated embodiment, is a biconvex lens made of silicone, PMMA, hydrogel or the like. It is implanted subsequent to implantation of annular member 30 and is preferably made to have at least a limited degree of compressibility to allow insertion through the same incision. Typically, such a lens would have a diameter of about 3.0 mm to about 8.0 mm. After being positioned in the opening formed by annular member 30, and removal of the implantation tool, lens member 32 will expand to be held in place by annular member 30 and posterior capsule 10.

The components of this embodiment of the invention are shown to a larger scale in FIGS. 2 and 3. As is shown in FIG. 2, the outer periphery of annular member 30 has the form of an annular ring 40 which will be seated in the fornix between posterior capsule 10 and the remaining portions 12 of the anterior capsule. In the preferred embodiment, ring 40 has a larger cross section than planer section 48. Typically, member 30 has a diameter of 9.0 mm to 9.5 mm, while section 48 has a thickness of about 0.5 mm to 1.0 mm.

In one embodiment, member 30 is formed to present, adjacent its inner periphery, a transparent region 42 which is configured as a bifocal lens portion which will focus, or aid in focusing, on the retina, light rays entering the eye at angles which are offset from the optical axis of the ocular system. Region 42 may be configured to have a refractive power which varies. Either the entirety of member 30, or region 42, can be made of a transparent material.

The inner periphery 44 of member 30 is configured to mate with the contacting surface of lens member 32 when the latter is in its implanted condition. Therefore, the curvature of the anterior surface 46 of portion 42 will be selected in dependence on the curvature of surface 44 and the refractive power which region 42 is to have. It is desired that the curvature of section 46 and inner periphery 44 are selected such that lens 32 has $+3$ to $+4$ diopter power in region 42. In this manner, a blended bifocal is achieved The diameter of annular member 30 is selected to correspond to that of the capsular bag, which, in most individuals is of the order of 9.5 mm. The diameter at the inner periphery of member 30, at the meeting line between surfaces 44 and 46, is preferably of the order of 3.5 mm.

Figure 7:
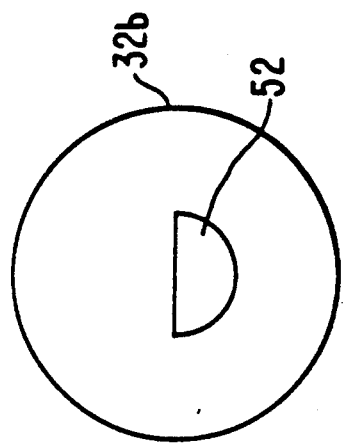
FIGS. 6 and 7 are front views of different lenses according to the present invention.
Figure 6:
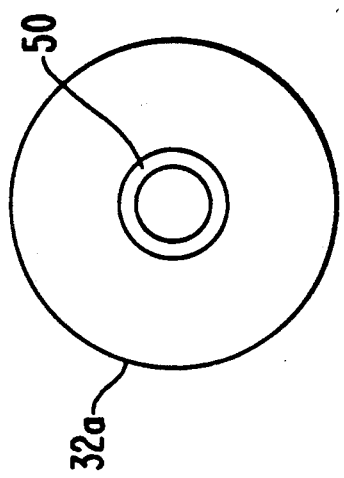

As shown in FIG. 3, lens member 32 may have a conventional biconvex configuration and a diameter of the order of 3-4 mm. For implantation via an incision having a length of the order of 3 mm, this lens need be compressed by only a small amount. Lens member 32 may be made of silicone PMMA, or hydrogel. Other materials may be used, provided that they impart to lens member 32 the property of being at least slightly compressible and of automatically assuming the desired final shape after removal of the implantation tool. While lens 30 can be made as illustrated in FIG. 3, other configurations where the bifocal or other lens component is made part of the lens itself is also within the scope of this invention. In that regard, other lens configurations for lens 32 are illustrated in FIGS. 6 and 7. In FIG. 6, lens 32a is provided with an annular bifocal or other lens component 50, while in FIG. 7 lens 32b has bifocal or other lens component 52 in the form of a semicircular disc. Yet other lenses, such as Fresnel and aspherical, are also within the scope of this invention.

To further clarify the structure of the embodiment shown in FIGS. 2 and 3, a plan view thereof is shown in FIG. 4, which is to a smaller scale than FIGS. 2 and 3. In FIG. 4, the outline of lens member 32 is shown in broken lines, and the radial extent of region 42 is indicated. FIG. 4 particularly illustrates that annular ring 40 and region 42 are both continuous in the circumferential direction and are joined together by a solid, or continuous, annular portion 48 so that no openings or discontinuities exist between the inner and outer peripheries of member 30.

A second embodiment of the invention is illustrated in FIG. 5, this embodiment differing from that of FIGS. 2–4 only with respect to the configuration of annular member 30' in the region of its inner periphery 44'. In the embodiment shown in FIG. 5, the inner periphery 44' of annular member 30' forms a groove, or pocket, enabling lens member 32 to be securely gripped at its periphery, and thus held in a defined position in chamber 24. More specifically, portions of the inner periphery 44' of annular member 30' mate with peripheral portions of the anterior and posterior surfaces of lens member 32. Here again, region 42' adjacent inner periphery 44' provide a lens portion having a higher lens power than the remainder of lens member 32 so as to form a bifocal lens. Also illustrated is the fact that a section 48' of member 30' can be formed to extend at an angle $\alpha =$ about 10° relative to the plane of the central part of member 30' for ease of insertion. When member 30' has the curved formed shown in broken lines in FIG. 5, it will be implanted in the eye with an orientation which places lens 32 closer to iris 6 (FIG. 1).

In each embodiment of the invention, the inner periphery of annular member 30, 30' is configured to mate with the associated surface or surfaces of lens member 32 so that no gap is present between the two members and no fluid can seep therebetween.

For example, lens 32 can be made such that it expands into place. Alternately, it can be snap-fit into position, and can include means for firmly joining lens 32 to member 30, 30' to help achieve firm fixation. As can be seen, member 30, 30' covers the entire capsular bag. This helps reduce the liklihood of capsular opacification (cellular growth) in the posterior capsule. Further still, because member 30, 30' is disc-shaped, a circular tension is applied to the bag. This can help reduce tears extension or wrinkles to the bag associated with many prior art devices.

While the description above refers to particular embodiments of the present invention, it will be understood that many modifications may be made without departing from the spirit thereof. For example, lens member 32 and annular member 30 can be configured without member 32 acting as a bifocal lens. Further, other means can be used to join lens member 32 to annular member 30, so as to still permit member 30 to be foldable and inserted through a very small incision, but without a need to fold the optical element 32. Further still, ring 40 can include other elements such as flexible hooks, support loops or the like to hold member 30 in proper position in the eye. Accordingly, the accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An implantable intraocular lens assembly comprising:
   a first member having an annular form, an outer periphery and an inner periphery delimiting an opening; and
   a second member of transparent material having at least one curved surface and an outer periphery;

wherein: said second member is separated from said first member before implantation and is inserted into said opening of said first member after implantation of said first member, and wherein: said first member has an optical region adjacent said inner periphery and configured such that said optical region and said second member together constitute an optical converging lens.

2. An assembly as defined in claim 1 wherein said optical converging lens has a lens power which has different valves at different locations across said lens.

3. An implantable intraocular lens assembly comprising:
   a first centering member having a disc-like annular form with an outer periphery having a diameter of about 9 mm to about 9.5 mm and an inner periphery delimiting an opening, said first member being foldable such that it can be passed through a 3 mm incision in an eye; and
   a second lens member of transparent material having at least one curved surface and an outer periphery, said second member being compressible such that it can be passed through a 3 mm incision in an eye;
   wherein: said second member is separated from said first member before implantation and is inserted into said opening of said first member after implantation of said first member.

4. An assembly as defined in claim 3 wherein said second member is made of a material selected from the group consisting of silicone and hydrogel.

5. An assembly as defined in claim 4 where said first member is made of silicone.

6. An assembly as defined in claim 3 where the outer periphery of said first member has a raised, ring-like configuration.

7. An assembly as defined in claim 3 further including means for removably joining said first member to said second member.

8. An assembly as defined in claim 3 wherein the inner periphery of said first member defines an annular groove into which said second member is matingly joined, and locked into place.

9. An assembly as defined in claim 3 wherein at least a portion of said first member has an arcuate configuration.

10. An assembly as defined in claim 3 wherein at least a portion of said inner periphery of said first member has a configuration matching that of a portion of said second member adjacent said outer periphery of said second member.

11. An assembly as defined in claim 10 wherein said second member has two opposed surfaces which meet at said outer periphery of said second member, and said inner periphery of said first member has the form of a groove configuration to receive said outer periphery of said second member when said second member is inserted into the opening of the first member.

12. An assembly as defined in claim 3 wherein said disc-like configuration is curved adjacent its outer periphery.

13. A method of implanting the lens assembly defined in claim 3 into a posterior chamber of an eye via an incision formed in the cornea, said method comprising:
   forming an incision in the cornea of approximately 3 mm in length;
   folding the first member such that it passes through the incision;
   unfolding the first member and implanting it into the posterior eye chamber so that the first member is held in position in the posterior eye chamber via its outer periphery;
   after implantation of the first member, compressing the second member such that it too passes through the incision; and
   permitting the second member to expand such that it is implanted into the opening delimited by the inner periphery of the first member so that the outer periphery of the second member engages the inner periphery of the first member.

14. A method as defined in claim 13 wherein the first member is implanted in a capsular Fornix provided in the posterior chamber of the eye.

* * * * *